United States Patent [19]

Yee et al.

[11] 4,208,501
[45] Jun. 17, 1980

[54] CARBAZOLYL DIACETYLENIC POLYMERS

[75] Inventors: Kwok C. Yee, Randolph; Ronald R. Chance; Ray H. Baughman, both of Morris Plains, all of N.J.

[73] Assignee: Allied Chemical Corporation, Morris Township, Morris County, N.J.

[21] Appl. No.: 929,062

[22] Filed: Jul. 28, 1978

Related U.S. Application Data

[62] Division of Ser. No. 772,190, Feb. 25, 1977, Pat. No. 4,125,534.

[51] Int. Cl.² .......................................... C08F 126/06
[52] U.S. Cl. .............................. 526/259; 204/159.22; 260/315; 430/80; 252/301.17; 252/600
[58] Field of Search ........................................ 526/259

[56] References Cited

U.S. PATENT DOCUMENTS

| | | | |
|---|---|---|---|
| 3,647,428 | 3/1972 | Ono et al. | 526/259 |
| 3,764,316 | 10/1973 | Dailey et al. | 526/259 |

Primary Examiner—Harry Wong, Jr.
Attorney, Agent, or Firm—David W. Collins; Robert J. North

[57] ABSTRACT

Novel carbazolyl diacetylenic monomers and polymers are provided. The monomers have the structure

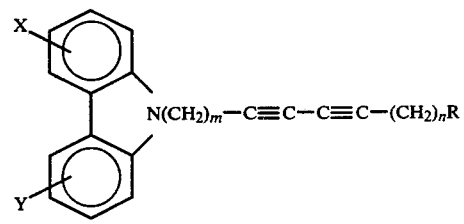

where "m" and "n" are integers of from 0 to 10, X and Y are independently selected from the group consisting of —H, —Cl, —Br and —NO and R is a member selected from the group consisting of —CH$_3$, —OH, —O-CONHR' and

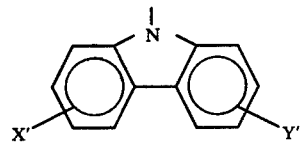

where R' is an alkyl, aryl or ester derivative and X' and Y' are independently selected from the group consisting of —H, —Cl, —Br and —NO. The monomers are conveniently prepared by oxidative coupling of terminated carbazolyl acetylenes, by cross coupling of bromoacetylenes with terminal acetylenes, or by substitution reaction of alkali carbazolides with the appropriate diacetylenes. The polymers are prepared by 1,4-addition reaction of the corresponding monomers in the solid state. The polymers are particularly useful as photoconductors and as non-linear optical materials. The monomers are useful as high energy radiation dosage indicators.

16 Claims, No Drawings

CARBAZOLYL DIACETYLENIC POLYMERS

CROSS-REFERENCES TO RELATED APPLICATIONS

This application is a divisional application of parent U.S. Application Ser. No. 772,190, issued Feb. 25, 1977, which issued as U.S. Pat. No. 4,125,534, on Nov. 14, 1978.

BACKGROUND OF THE INVENTION

1. Field of the Invention

This invention relates to diacetylenic monomers and polymers and, more particularly, to carbazolyl diacetylene and its derivatives, useful as photoconductive and non-linear optical materials and as high energy radiation dosage indicators.

2. Description of the Prior Art

In the development of photoreceptors for use in commercial imaging systems such as electrophotography, the importance of organic polymer materials has rapidly increased due to cost considerations and the wide range of obtainable properties. Consequently, there has been recent interest in the photoelectronic properties of organic polymers. For practical use over a wide range of operational conditions, the materials must be able to form a film having a large area, have a high resolution of the image and maintain mechanical integrity. It has long been recognized that among many organic solids, amorphous poly-N-vinylcarbazole (PVK), in which the carbazolyl groups are attached to a carbon-carbon single bond polymer backbone, is an important photoconductor. At the present time, PVK has been successfully utilized as a material for electrophotography. However, while this material is very useful, new materials having even more exceptional properties are required to further increase the efficiency of imaging systems.

Frequency tripling (or doubling) using non-linear optical devices is important in order to obtain high power laser sources in frequency ranges such as the ultraviolet and near-infrared where conventional high power laser sources are unavailable. Certain polydiacetylenes have been shown to have the highest third order susceptibilities ($X^{(3)}$) known for materials with a comparable transparency range in the near-infrared; see Vol. 36, *Physical Review Letters*, pp. 956–959 (1976). These third order susceptibilities are comparable in magnitude to those found for germainum. However, germanium is not usable at wavelengths below 2 μm, while the polydiacetylenes are usable down to about 0.5 μm. Compositions possessing even higher third order susceptibilities usable at such short wavelengths are desired.

Since high energy irradiation has become an economically viable means of sterilization, reliable radiation dosage indicators are required. Many diacetylenes are known to react upon exposure to gamma ray irradiation, that is, they undergo a color change indicating polymerization. However, the response is usually gradually developed and an instrument (e.g., a spectrophotometer) is generally required for determining dosage. Compositions capable of sharp, visual indication at some threshold dosage of radiation are desired.

SUMMARY OF THE INVENTION

In accordance with the invention, carbazolyl diacetylene and its derivatives are provided. The carbazolyl diacetylenic compounds have the formula

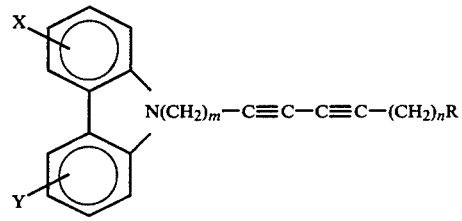

where "m" and "n" are integers of from 0 to 10, X and Y are independently selected from the group consisting of —H, —Cl, —Br and —NO and R is a member selected from the group consisting of —CH₃, —OH, OCONHR' and

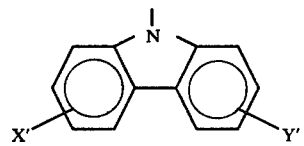

where R' is an alkyl, aryl or ester derivative and X' and Y' are independently selected from the group consisting of —H, —Cl, —Br and —NO. The diacetylenic compounds of the invention are conveniently prepared by oxidative coupling of terminated carbazolyl acetylenes, by cross coupling of bromoacetylenes with terminated acetylenes, or by substitution reaction of alkali carbazolides with the appropriate diacetylenes.

Also in accordance with the invention, polymers of the foregoing carbazolyl diacetylenic monomers are provided. These polymers are most conveniently prepared by 1,4-addition reaction of the corresponding monomers in the solid state. The polymers of the invention evidence high carrier mobilities compared with the prior art PVK compound. These improved photoconductive properties, coupled with high mechanical strength, unique thermomechanical properties and excellent thermal stability, make the polymers of the invention attractive candidates for various photoconductivity applications. The polymers also evidence lower bandgaps than prior art polydiacetylenes and, hence, higher third order susceptibilities than prior art polydiacetylenes, making them particularly useful in non-linear optical applications. Finally, the monomers exhibit a visual, non-linear response to high energy irradiation, making them useful as radiation dosage indicators.

DETAILED DESCRIPTION OF THE INVENTION

1. Synthesis of Carbazolyl Diacetylenic Monomers

The synthesis of carbazolyl diacetylenic monomers (I) having the structure

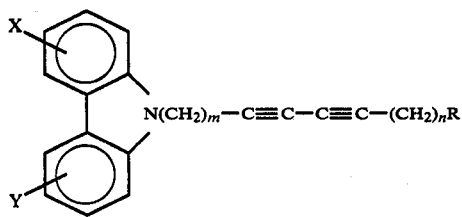

$$N(CH_2)_m-C\equiv C-C\equiv C-(CH_2)_nR \quad (I)$$

is given below, where "m" and "n" are integers of 0 to 10, X and Y are independently selected from the group consisting of —H, —Cl, —Br and —NO, and R is a member selected from the group consisting of —CH$_3$, —OH, —OCONHR' and

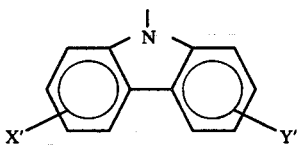

where R' is an alkyl, aryl or ester derivative and X' and Y' are independently selected from the group consisting of —H, —Cl, —Br and —NO.

Alkyl derivatives are —C$_r$H$_{2r+1}$, such as —C$_2$H$_5$, —C$_8$H$_{17}$ and —C$_{18}$H$_{37}$. Aryl derivatives, for example, are substituted phenyls and naphthyls, such as —C$_6$H$_5$, —C$_6$H$_4$-p-CH$_3$ and —C$_{10}$H$_7$. Ester derivatives, for example, are —CH$_2$OCOC$_s$H$_{2s+1}$, such as —CH$_2$OCOC$_2$H$_5$ and —CH$_2$OCOC$_4$H$_9$.

While compositions in which X, Y, X' and Y' are all H are useful materials in photoconductive and other applications, electron withdrawing substituents, such as halogens and —NO, enhance the photoconductive properties of polymers of the monomers. Accordingly, such substituents are preferred.

Examples of monomers of the invention include:
1. Cz—C≡C—C≡C—Cz
   1,4-di-(N-carbazolyl)-1,3-butadiyne
2. Cz—CH$_2$—C≡C—C≡C—CH$_2$—Cz
   1,6-di-(N-carbazolyl)-2,4-hexadiyne
3. Cz—(CH$_2$)$_3$—C≡C—C≡C—(CH$_2$)$_3$—Cz
   1,10-di-(N-carbazolyl)-4,6-decadiyne
4. Cz—CH$_2$—C≡C—C≡C—(CH$_2$)$_4$OCONHC$_{18}$H$_{37}$
   9-(N-carbazolyl)-5,7-nonadiyn-1-ol octadecylurethane
5. Cz—CH$_2$—C≡C—C≡C—(CH$_2$)$_4$OCONHC$_{12}$H$_{25}$
   9-(N-carbazolyl)-5,7-nonadiyn-1-ol dodecylurethane
6. Cz—CH$_2$—C≡C—C≡C—(CH$_2$)$_4$OCONHC$_8$H$_{17}$
   9-(N-carbazolyl)-5,7-nonadiyn-1-ol octylurethane
7. Cz—CH$_2$—C≡C—C≡C—(CH$_2$)$_4$OCONHC$_6$H$_{13}$
   9-(N-carbazolyl)-5,7-nonadiyn-1-ol hexylurethane
8. Cz—CH$_2$—C≡C—C≡C—(CH$_2$)$_4$OCONHC$_4$H$_9$
   9-(N-carbazolyl)-5,7-nonadiyn-1-ol butylurethane
9. Cz—CH$_2$—C≡C—C≡C—(CH$_2$)$_4$OCONHC$_2$H$_5$
   9-(N-carbazolyl)-5,7-nonadiyn-1-ol ethylurethane
10. Cz—CH$_2$—C≡C—C≡C—(CH$_2$)$_4$OCONHCH$_3$
    9-(N-carbazolyl)-5,7-nonadiyn-1-ol methylurethane
11. Cz—CH$_2$—C≡C—C≡C—(CH$_2$)$_4$OCONHCH$_2$OCOC$_2$H$_5$
    9-(N-carbazolyl)-5,7-nonadiyn-1-ol ethoxycarbonylmethylurethane
12. Cz—CH$_2$—C≡C—C≡C—(CH$_2$)$_4$OCONHCH$_2$OCOC$_4$H$_9$
    9-(N-carbazolyl)-5,7-nonadiyn-1-ol butoxycarbonylmethylurethane
13. Cz—CH$_2$—C≡C—C≡C—(CH$_2$)$_4$OCONH—C$_6$H$_4$—p-CH$_3$
    9-(N-carbazolyl)-5,7-nonadiyn-1-ol p-tolylurethane
14. Cz—CH$_2$—C≡C—C≡C—(CH$_2$)$_4$OCONH—C$_6$H$_4$—m-CH$_3$
    9-(N-carbazol)-5,7-nonadiyn-1-ol m-tolylurethane
15. Cz—CH$_2$—C≡C—C≡C—(CH$_2$)$_4$OH
    9-(N-carbazolyl)-5,7-nonadiyn-1-ol

16.

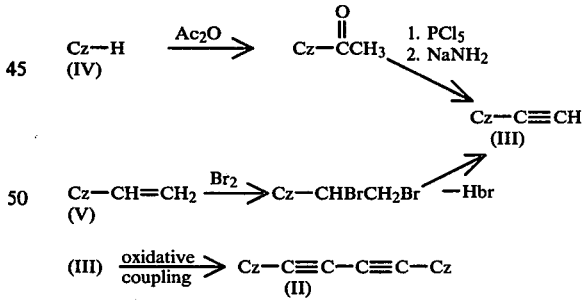

1,6-bis(N-3-bromocarbazolyl)-2,4-hexadiyne

17. Cz—CH$_2$—C≡C—C≡C—(CH$_2$)$_{11}$CH$_3$
    1-(N-carbazolyl)-2,4-heptadecadiyne Cz in the above formulas represents the carbazolyl group, whether substituted or unsubstituted.

For n=m=0 and R=Cz, the desired dicarbazolyl diacetylene (II) below is prepared by oxidative coupling of N-carbazolylethyne (III) which, in turn, is prepared by well-known methods from either carbazole (IV) or N-vinyl-carbazole (V):

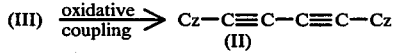

For m=n≧1 and R=Cz, the desired dicarbazolyl diacetylene (VI) below is prepared either by (1) oxidative coupling of terminated carbazolyl acetylene (VII) which, in turn, is prepared by a reaction of alkali carbazolide (M$^+$Cz$^-$) with linear acetylene (VIII) which has a good leaving group (L) such as tosylate (TsO—) or halogen (—Cl, —Br) on the chain end or by (2) substitution reaction of alkali carbazolide with a diacetylene (IX) which, in turn, is prepared from the corresponding acetylene (VIII) by oxidative coupling or from diacetylenediol by well-known methods:

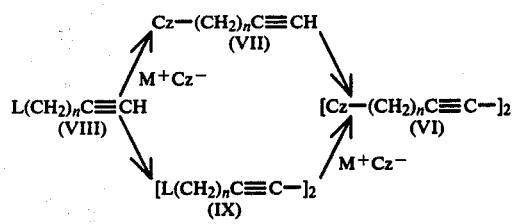

For example, 1,6-dicarbazolyl-2,4-hexadiyne (DCHD) is prepared from carbazole in almost quantitative yield by the following route: Carbazole (1) reacts with sodium amide in liquid ammonia to give sodium carbazolide (2) which, in turn, reacts with 3-bromopropyne, giving rise to 3-(N-carbazolyl)-1-propyne (3) with an overall yield of about 90 to 95%.

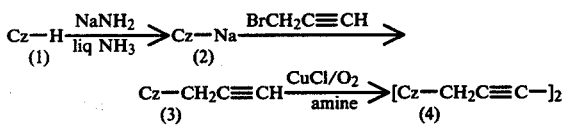

The desired diacetylene DCHD (4) is then obtained in about 95% yield by oxidative coupling of (3).

Alternately, for m≠n and R≠Cz, the unsymmetrical carbazolyl diacetylene (X) is synthesized by cross coupling of bromoacetylene (XI) and terminated acetylene (XII)

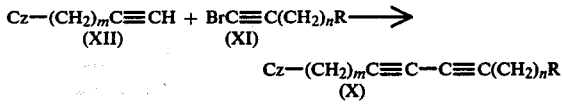

For example, 9-(N-carbazolyl)-5,7-nonadiyn-1-ol (5) is synthesized in about 80% yield by cross coupling of 3-(N-carbazolyl)-1-propyne (3) with 6-bromo-5-hexyn-1-ol (6), which, in turn, is synthesized from 5-hexyn-1-ol with sodium hypobromite. Reaction of (5) with methylisocyanate (7) gives 9-(N-carbazolyl)-5,7-nonadiyn-1-ol methylurethane (8) in almost quantitative yield.

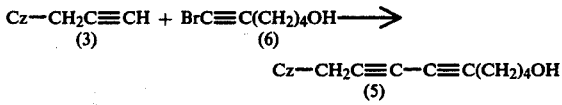

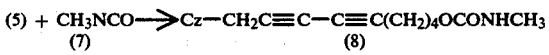

2. Synthesis of Carbazolyl Diacetylenic Polymers

The formation of polydiacetylenes (XIII) from the corresponding monomer (I) is given below. The polydiacetylenes of the invention have the structure

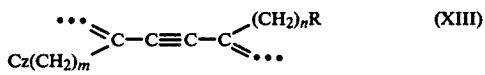

where "m" and "n" are integers of 0 to 10, Cz is the carbazolyl group, whether substituted or unsubstituted, and R is a substituent group, all as defined above. Alternatively, the electronic structure of the backbone can be written as the mesomeric butatriene structure

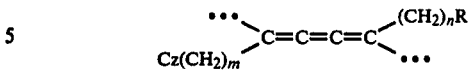

In general, resonance contributions are made from both these structures.

Polymerization proceeds by 1,4-addition reaction of the monomer in the solid state, employing actinic radiation (visible wavelength or shorter), heat or mechanical stress. Irradiation with ultraviolet light or γ-rays is a convenient method for effecting solid state polymerization. A convenient source of γ-radiation is a $Co^{60}$ source. Polymers having relatively inflexible substituent groups ("m" and "n" both small) typically are both insoluble in common organic solvents and infusible. With increasing values of "m" and "n", however, both solubility and fusibility of the resulting polymers tend to increase. The polymer crystals are strongly dichroic, with the axis of dichroism substantially parallel to a rapid growth direction of the monomer phase, indicating that the fully conjugated chains of the polymer are highly aligned, an aspect which is important for optimization of properties. The infrared spectra of the polymers are essentially identical to those of the corresponding monomers, indicating that the polymers possess the same functionality as the corresponding monomers. Raman spectral evidence indicates that 1,4-addition reaction in the solid state has occurred at the diacetylenic group within the monomer molecule. The Raman intense vibration at about 2260 $cm^{-1}$, which is characteristic of the diacetylenic functionality in the monomer, disappears during polymerization and is replaced by Raman intense vibrations between 1450 to 1540 $cm^{-1}$ ($\nu_{C=C}$) and between 2060 to 2140 $cm^{-1}$ ($\nu_{C\equiv C}$) in the polymer, corresponding to the multiple bond vibrations from the conjugated backbone. This spectral evidence, together with the X-ray diffraction results showing the expected 4.9 Å (or multiple thereof) chain repeat distance, confirm that solid state polymerization has proceeded by 1,4-addition reaction.

For example, crystallization of 1,6-dicarbazolyl-2,4-hexadiyne (DCHD) from common organic solvents such as acetone, benzene, toluene or N,N-dimethylacetamide gives colorless, long needle crystals which can be polymerized to about 100% yield by γ-irradiation (such as 50 Mrad dosage at 1 Mrad/hr), by thermal annealing (such as 110° C. for 2 wks) or by mechanical stress (such as 16 tons/in² at a temperature of about 220° C. for about 2 min). The resulting polymer (poly-DCHD) is in the form of gold fibers with metallic brilliancy. Elemental analyses show that the poly-DCHD has the correct composition. The infrared spectrum of the polymer is practically identical to that of the monomer. Raman spectral evidence shows that the polymer exhibits a new band for $\nu_{C\equiv C}$ at 2086 $cm^{-1}$, while the $\nu_{C=C}$ band for the monomer at 2257 $cm^{-1}$ disappears. X-ray single crystal analyses show that polymers obtained by either thermal annealing or γ-irradiation are 90–100% crystalline and have practically the same cell parameters. The polymer crystals are monoclinic and the repeat distance along the polymer chain is 4.9 Å. These results indicate that the reaction has proceeded by 1,4-addition polymerization.

For symmetrically substituted carbazolyl polydiacetylenes where "m" and "n" are both equal and are integers of 0 to 4 and where R is Cz, energy transfer from the polarizable groups (the carbazolyl groups) to the polymer backbone is facilitated. Such low values of "m" and "n", coupled with two carbazolyl groups per monomer unit, provide more efficient energy transfer and hence, superior photoconduction. Accordingly, such compositions are preferred.

A competing factor in the selection of the values of "m" and "n" is that higher values of "m" and "n" provide better melt and solution processability, permitting films of the polymer to be prepared more readily. However, an alternate method for preparing polymer films is more generally feasible. The precursor monomer is deposited on a substrate via conventional solution, melt or vapor deposition methods. The resulting film is then polymerized directly on the substrate, employing the foregoing techniques. This latter method does not require melt and solution processability of the polymer in order to obtain polymer films.

For single crystals of poly-DCHD, the carrier mobility is about 1 cm$^2$/volt-sec, as compared with a carrier mobility of about $10^{-7}$ cm$^2$/volt-sec, for PVK. In addition, poly-DCHD exhibits a highly desirable red shift in the photoconductivity action spectrum compared to other polydicacetylenes, which typically evidence photoconduction only in the ultraviolet region. Poly-DCHD shows a peak in the photoductivity action spectrum at about the same excitation wavelength (370 nm) as PVK. In contrast, prior art polydiacetylenes, such as poly-2,4-hexadiyne-1,6-diol bis(p-toluene sulfonate), typically evidence peaks at about 250 to 290 nm. The photoconduction onset (the photon energy at which the photocurrent is 10% of its peak value) for poly-DCHD (single crystal) is at 2.3 eV, compared with the location of the lowest energy absorption band at 1.9 eV. In contrast, prior art polydiacetylenes typically evidence photoconduction onset at about 2.7 eV or higher (for single crystals) or 3.1 eV or higher (for films).

In general, the photocurrent in a film is much less than that in a crystal. However, photocurrents in films of unsymmetrically substituted carbazolyl polydiacetylenes are at least one order of magnitude greater than those in films of poly-5,7-dodecadiyn-1,12-diol-bis-methylurethane or poly-5,7-dodecadiyn-1,12-diol-bis-phenylurethane.

The polymers of the invention further evidence good mechanical strength, attractive thermo-mechanical behavior and excellent thermal stability. For example, poly-DCHD crystals evidence an ultimate tensile strength of about 130,000 psi, and only 0.5% weight loss at 300° C. In addition to high structural perfection and high thermal stability, these crystals evidence a reversible thermal contraction in the chain direction with increasing temperature from −50° to 300° C.

The carbazolyl polydiacetylenes of the invention have the smallest bandgap ($E_g$=1.88 eV) of any known polydiacetylene. Since the third order susceptibility $\chi^{(3)}$ varies as $E_g^{-6}$, then $\chi^{(3)}$ for the compounds disclosed herein is calculated to be at least about 50% higher than those measured for prior art polydiacetylenes, with little sacrifice of transparency range. Equally important for laser applications is the unusual high thermal stability of the carbazolyl polydiacetylenes of the invention, as exemplified by poly-1,6-di-(N-carbazolyl)-2,4-hexadiyne. Also, several of the unsymmetrically substituted carbazole compounds, such as poly-9-(N-carbazolyl)-5,7-nonadiyn-1-ol methylurethane, show non-centric space groups which, for similar reasons, make them suitable for frequency doubling via second harmonic generation.

Finally, some of the carbazolyl diacetylenic monomers of the invention evidence a visual, non-linear response to high energy irradiation. A substantial induction period is observed in that up to a particular dosage, little reaction occurs. However, upon exposure to a few additional Mrads, near-quantitative conversion is achieved. For example, 1,6-di-(N-carbazolyl)-2,4-hexadiyne monomer shows little conversion to the corresponding polymer up to dosages of 10 Mrad by Co$^{60}$ γ-rays. However, dosages of 12 Mrad result in 78% conversion to polymer, while dosages of 15 Mrad result in 98% conversion. Such behavior is important for the design of radiation dosage indicators which provide a sharp color change upon exposure to a critical radiation dosage.

EXAMPLES

EXAMPLE 1

Synthesis of 1,4-di-(N-carbazolyl)-1,3-butadiyne Monomer and Polymer

Synthesis of 1,4-di-(N-carbazolyl)-1,3-butadiyne monomer was carried out by first preparing N-acetylcarbazole from carbazole and acetic anhydride. The N-acetylcarbazole was then reacted over PCl$_5$ to produce N-(1,2-dichloroethenyl) carbazole, which was then reacted with sodium amide in liquid ammonia to give N-carbazolylethyne. The ethyne was then oxidatively coupled over cuprous chloride to give 1,4-di-(N-carbazolyl)-1,3-butadiyne. Details of the reaction are given below.

A. Preparation of N-acetylcarbazole

A 500 ml, 3-necked, round bottom flask was fitted with mechanical stirrer, reflux condenser and means for providing nitrogen atmosphere. To the flask was added 30 g (0.18 mole) of carbazole, 24.6 g (0.18 mole) of finely powdered zinc chloride, and 55 g (0.54 mole) of acetic anhydride. The resulting mixture was stirred and heated with an oil bath of 80° C. for 10 minutes. The reaction mixture was then poured into 1200 ml of ice water. After stirring for 2 hrs, the precipitate was collected by filtration, washed five times with 100 ml portions of water and dried, resulting 37 g (99% yield) of solid. Recrystallization of the crude product (37 g) from ethanol (185 ml) gave 22 g (59% yield) of the desired product, m.p. 71.2°–72.2° C. (IR (KBr pellet): 1680 cm$^{-1}$ (C=O).

B. Preparation of N-(1,2-dichloroethenyl)carbazole

A 500 ml, 3-necked, round bottom flask was fitted with mechanical stirrer, reflux condenser and means for providing nitrogen atmosphere. To the flask was added 20.9 g (0.10 mole) of N-acetylcarbazole (from Example 1A), 43.2 g of phosphorus pentachloride and 150 ml of dry benzene. The resulting mixture was stirred and heated to reflux for 24 hrs, cooled and poured into 300 ml of ice water. After stirring for about 30 min, the mixture was extracted with 150 ml of benzene. The benzene layer was washed five times with 150 ml portions of water, dried and concentrated, resulting in 25 g of a viscous, dark-red liquid. The crude product (25 g) was crystallized from methanol (50 ml) with activated charcoal, giving 14.3 g of desired product, m.p. 51°–53° C. IR (KBr pellet): 3040 cm$^{-1}$ (Ar H), 1590 cm$^{-1}$ (C=C).

C. Preparation of N-carbazolylethyne

A 2,000 ml, 3-necked, round bottle flask was fitted with mechanical stirrer, thermometer, addition funnel and means for providing nitrogen atmosphere. To the flask was added 6.8 g (0.174 mole) of sodium amide and 1000 ml of liquid ammonia. The resulting mixture was stirred at $-33°$ C., and a solution of 8.9 g (0.034 mole) of N-(1,2-dichloroethenyl)carbazole (from Example 1B) in 40 ml of dry ether was added dropwise over a period of 70 min. After stirring at $-33°$ C. for an additional 5.5 hrs, the ammonia was allowed to evaporate. To the reaction mixture was added 200 ml of ethyl ether. The resulting mixture was poured into 200 ml of ice water. The aqueous layer was extracted four times with 100 ml portions of ethyl ether. The combined ether layers were washed twice with 100 ml portions of water, dried and concentrated, resulting in 6 g (93% yield) of brown solids. The brown solids were extracted five times with 100 ml portions of petroleum ether (b.p. $60°-110°$ C.). Concentration of the petroleum ether solution gave 4.5 g of desired product, m.p. $60°-62°$ C. IR (KBr pellet) in $cm^{-1}$: 3280 (C≡CH), 2180 (C≡C), 1620+1600 (C═C), 1445+1340 (C—N), 745+720 (Ar), 660 (C≡CH).

D. Synthesis of 1,4-di-(N-carbazolyl)-1,3-butadiyne

A 100 ml, 3-necked, round bottom flask was fitted with mechanical stirrer, addition funnel, reflux condenser and oxygen bubbler. To the flask was added with 3.4 g (0.035 mole) of cuprous chloride, 5.6 g (0.104 mole) of ammonium chloride, and 15 ml of water. The resulting mixture was stirred, and oxygen was bubbled through the mixture. A solution of 2.6 g (0.014 mole) of N-carbazolylethyne (from Example 1C) in 15 ml of 1,2-dimethoxyethane was added dropwise over a period of 10 mins. A slight exothermic reaction was observed. After oxygen bubbling and stirring for 23 hrs at room temperature, the reaction mixture was extracted four times with 200 ml portions of benzene. The combined benzene extracts were dried and concentrated, resulting in 2.7 g of solid materials. Recrystallization of the crude product (2.7 g) from 100 ml of toluene gave 2.2 g (84% yield) of crystals. These crystals did not melt upon heating to $300°$ C. from $25°$ C., but turned dark at about $240°$ C. IR (KBr pellet) in $cm^{-1}$: 3025 (Ar H), 2175 (C≡C), 1620+1600+1580 (C═C), 1440+1330 (C—N), 740+720 (Ar). Anal: calculated for $C_{28}H_{16}N_2$: C, 88.40%; H, 4.24%; N, 7.36%; found: C, 87.14%; H, 4.43%; N, 6.98%. Mass spectrum: molecular ion was observed at m/e 380, compared with a calculated value of 380.

E. Polymerization of 1,4-di-(N-carbazolyl)-1,3-butadiyne by Thermal Annealing About 0.23 g of light tan crystals (crystallized from toluene) of 1,4-di-(N-carbazolyl)-1,3-butadiyne (from Example 1D) was sealed in a glass tube under reduced pressure (0.1 mm). The contents were heated at $216°$ C. for 24 hr, giving rise to a black mass. The resulting mixture was then extracted with 100 ml of toluene, providing 0.12 g (52% of conversion) of black polymer.

EXAMPLE 2

Synthesis of 1,6-di-(N-carbazolyl)-2,4-hexadiyne Monomer and Polymer

The synthesis of 1,6-di-(N-carbazolyl)-2,4-hexadiyne monomer was carried out by first preparing 3-(N-carbazolyl)-1-propyne from sodium carbazolide and 3-bromo-1-propyne. The propyne was then oxidatively coupled over cuprous chloride to give the desired hexadiyne. The monomer was then variously polymerized by γ-irradiation, thermal annealing and mechanical stress. Details of the reactions are given below.

A. Preparation of 3-(N-carbazolyl)-1-propyne

A 3,000 ml, 3-necked, round bottom flask was fitted with mechanical stirrer, addition funnel, Dry Ice/acetone reflux condenser and means for providing nitrogen atmosphere. To the flask was added 75 g (0.45 mole) of carbazole, 20 g (0.50 mole) of sodium amide, and 1500 ml of liquid ammonia. After stirring vigorously at $-33°$ C. for about 2.5 hr, 75 g (0.63 mole) of 3-bromo-1-propyne was added dropwise over a period of 1 hr to the reaction mixture at $-55°$ C. After the addition, stirring was continued for an additional 5 hrs, and the ammonia was allowed to evaporate overnight. The residue in the reaction flask was extracted with hexane four times. In each extraction, 3,000 ml of hexane was used and the hexane mixture was stirred vigorously with a mechanical stirrer for about 5 hrs at room temperature. Removal of the solvent from each fraction gave the desired product: fraction #1=24 g (m.p. $94°-100°$ C.); fraction #2=21 g (m.p. $103°-106°$ C.); fraction #3=25 g (m.p. $104°-106°$ C.); and fraction #4=17 g (m.p. $100°-106°$ C.). The combined crystals (87 g, 94% yield) were recrystallized from hexane at a concentration of 7 g per 100 ml of hexane, giving 60 g of plate-like crystals, m.p. $104°-107°$ C. IR (KBr pellet) in $cm^{-1}$: 3250 (C≡CH), 2120 (C≡C), 1620+1590 (C═C), 1480 (CH$_2$), 1450+1320 (C—N), 740+720 (Ar), 680+660 (C≡CH). Anal: calculated for $C_{15}H_{11}N$: C, 87.77%; H, 5.40%; N, 6.82%; found: C, 88.01%; H, 5.54%; N, 6.57%.

B. Synthesis of 1,6-di-(N-carbazolyl)-2,4-hexadiyne

A 100 ml, 3-necked round bottom flask was fitted with mechanical stirrer, thermometer, addition funnel, oxygen bubbler and reflux condenser. To the flask was added 6.2 g (0.030 mole) of 3-(N-carbazolyl)-1-propyne (from Example 2A), 75 ml of dioxane, 0.3 g of N,N,N',N'-tetramethylethylenediamine, and 0.3 g of cuprous chloride. The resulting mixture was stirred vigorously, and oxygen was bubbled through the mixture. The reaction temperature went up to $48°$ C. from $32°$ C. within 10 min and then subsided. After stirring and bubbling oxygen to the mixture for an additional 2 hrs, the reaction mixture was concentrated to near dryness, and 40 ml of 0.6 N HCl solution was added. The resulting white precipitate was collected by filtration, washed four times with 50 ml portions of water, twice with 25 ml portions of methanol, twice with 25 ml portions of ethyl ether and dried, resulting in 5.9 g (96% yield) of white crystals. These crystals did not melt upon heating from room temperature to $300°$ C. at a heating rate of $10°$ C./min, but rather changed to a green-gold color with metallic brilliancy at $300°$ C. Crystallization from common organic solvents (such as acetone, benzene, toluene, and N,N-dimethylacetamide) gave colorless long needle crystals. IR (KBr pellet) in cm$^{-1}$: 3060 (Ar H), 2920 (CH), 1630+1600 (C=C), 1485 (CH$_2$), 1460+1325 (CN), 750+720 (Ar). Mass spectrum: molecular ion was observed at m/e 408, compared with a calculated value of 408. Anal: calculated for C$_{30}$H$_{20}$N$_2$: C, 88.20%; H, 4.94%; N, 6.86%; found: C, 88.18%; H, 5.13%; N, 6.69%.

C. Synthesis of Poly-1,6-di-(N-carbazolyl)-2,4-hexadiyne

Crystallization of 1,6-di-(N-carbazolyl)-2,4-hexadiyne (from Example 2B) from a common organic solvent (such as acetone, benzene, toluene, or N,N-dimethylacetamide) gave colorless, long needle crystals which were polymerized to almost quantitative yield by gamma irradiation, by thermal annealing, and by mechanical stress, as follows:

C1. Solid State Polymerization by Gamma Irradiation

About 0.266 g of colorless, long needle crystals of 1,6-di-(N-carbazolyl)-2,4-hexadiyne (crystallized from dioxane) was exposed to 50 Mrad of $\gamma$-radiation at a dose rate of 1 Mrad/hr, resulting in needle-like gold fibers with metallic brilliancy. Extraction of any unpolymerized monomer with 100 ml of hot dioxane for 5 hrs provided 0.264 g (99% conversion) of polymer. X-ray diffraction studies (Gandolfi camera) indicated that the sample was almost entirely crystalline. X-ray single crystal studies showed that the polymer crystals were monoclinic; the repeat distance along the polymer chain was 4.9 Å. IR (KBr pellet) in cm$^{-1}$: 3050 (Ar H), 2920 (CH), 1630+1600 (Ar C=C), 1490 (CH$_2$), 1455+1320 (CN), 745+720 (Ar). Anal: calculated for (C$_{30}$H$_{20}$N$_2$)$_x$: C, 88.20%; H, 4.94%; N, 6.86%; found: C, 88.26%; H, 5.07%; N, 6.54%.

In separate runs, 0.3 g samples of colorless long needle crystals (crystallized from toluene) were exposed to selected dosages of Co$^{60}$ $\gamma$-radiation at a dose rate of 1 Mrad/hr, resulting in the formation of the desired polydiacetylene (poly-1,6-di-N-carbazolyl-2,4-hexadiyne; poly-DCHD). Each irradiated sample was extracted with 200 ml of toluene at 60° C. overnight to remove any nonpolymer monomer from the mass, to yield the polymer in the amount indicated in Table I below.

Table I.

| Weight Percent of Irradiated Monomer Converted to Polymer | | | | | | | | | |
|---|---|---|---|---|---|---|---|---|---|
| Radiation Dosage, Mrad | | | | | | | | | |
| 1 | 10 | 12 | 14 | 15 | 16 | 20 | 40 | 50 | 80 |
| Wt. % | | | | | | | | | |
| 0 | 1.5 | 78 | 96.5 | 98 | 98.5 | 97.0 | 99.5 | 99.6 | 99.7 |

Examination of Table I shows that at the early stages of $\gamma$-irradiation (1 to 10 Mrad), the monomer crystals are only slightly solid state polymerizable. However, at dosages slightly greater than 10 Mrad, $\gamma$-irradiation produces a very fast rate of polymerization. Because of this unusual induction period in the $\gamma$-ray polymerization process, the DCHD monomer is useful as a radiation dosage indicator. No other prior art diacetylenes are known to exhibit this unusual behavior during irradiation polymerization.

The polymer fibers from which unreacted monomer had been extracted were highly dichroic, with the axis of dichroism coincident with the fiber direction. The 50 Mrad $\gamma$-irradiated fibers evidenced a tensile strength of about 133,000 psi and a modulus of about $5 \times 10^6$ psi.

C2. Solid State Polymerization by Thermal Annealing

About 0.228 g of colorless needle-like crystals of 1,6-di-(N-carbazolyl)-2,4-hexadiyne (crystallized from benzene) was sealed in an ampoule and heated at 110° C. for 205 hrs. The thermally annealed sample evidenced a metallic gold color. Extraction of the annealed sample with 200 ml of warm acetone for 3 hrs to remove any unpolymerized monomer resulted in 0.227 g (99.5% conversion) of gold-colored polymer. The infrared spectrum of this polymer was practically identical to the $\gamma$-irradiated polymer. Raman: $\gamma_{C\equiv C}=2086$ cm$^{-1}$ and $\gamma_{C=C}=1470+1455+1425$ cm$^{-1}$. Anal: calculated for (C$_{30}$H$_{10}$N$_2$)$_x$: C, 88.20%; H, 4.94%; N, 6.86%; found: C, 87.51%; H, 5.24%; N, 6.73%. Thermogravimetric analyses (Cahn balance, about 10 mg sample per run, programming at a 10° C./min rate, under argon) showed that the polymer was unusually stable, with practically no weight loss below 300° C.

C3. Solid State Polymerization by Mechanical Stress

About 1.1 g of finely powdered crystals of 1,6-di-(N-carbazolyl)-2,4-hexadiyne (crystallized from toluene) was subjected to compression by 16 tons/in$^2$ at a temperature of 220° C. for 2 mins, giving rise to a golden-colored film (2 inch in diameter) with metallic brilliancy. The surface of the film was quite smooth, although the film itself was brittle. About 0.313 g of the polymerized sample was extracted with 150 ml of hot dioxane for 3 hrs to remove any non-polymerized monomer, resulting in 0.307 g (98% conversion) of gold-colored polymer.

D. Photoconductive Properties of Poly-1,6-di-(N-carbazolyl)-2,4-hexadiyne

Carrier mobilities of single crystals of the polymer were measured using a pulsed photoconductivity measurement technique similar to that disclosed in Vol. 13, *Chemical Physics*, pp. 181–185 (1976). Mobilities similar to those reported therein (i.e., about 1 cm$^2$/volt-sec) were found for single crystals of poly-1,6-di-(N-carbazolyl)-2,4-hexadiyne.

Photoconductive action spectra showed a peak at about 370 nm, with photoconduction onset at about 2.3 eV.

EXAMPLE 3

Synthesis of 1,10-di-(N-carbazolyl)-4,6-decadiyne Monomer

The synthesis of 1,10-di-(N-carbazolyl)-4,6-decadiyne was carried out by first preparing 4,6-decadiyn-1,10-diol bis-(p-toluenesulfonate) from 4,6-decadiyn-1,10-diol and p-toluenesulfonyl chloride. The sulfonate was then reacted with sodium carbazolide to give the desired product. Details of the reaction are given below.

A. Synthesis of 4,6-decadiyn-1,10-diol bis-p-toluene sulfonate

A 250 ml, three-necked, round bottom flask was fitted with mechanical stirrer, thermometer and means for providing nitrogen atmosphere. To the flask was added 38.2 g (0.20 mole) of p-toluenesulfonyl chloride, 13.3 g (0.08 mole) of 4,6-decadiyn-1,10-diol and 150 ml of ether. The resulting mixture was stirred vigorously, and 56 g (1.00 mole) of freshly powdered potassium hydroxide was added over a period of 15 min at a temperature range of −5° to +2° C. After stirring at about 0° C. for an additional 1.5 hr, the reaction mixture was poured into 200 ml of ice-water. The resulting mixture was extracted three times with 100 ml portions of ether. The combined ethereal layers were washed twice with 100 ml portions of sodium bicarbonate solution, dried and concentrated, resulting in 32 g (84% yield) of white solids, m.p. 42°–44° C. Recrystallization from 50% ether/petroleum ether (30°–60° C.) at a concentration of 0.01 g/ml gave colorless fine needles, m.p. 43°–45° C. I.R. (KBr pellet) in cm$^{-1}$: 3080 (Ar—H stretching), 2980+2920 (CH stretching), 1600 (C═C stretching), 1370 (S—O), 1180 (S—O), 740 (Ar—H). Anal: calculated for $C_{24}H_{26}O_6S_2$: C, 60.74%; H, 5.52%; found: C, 60.06%; H, 5.63%.

B. Synthesis of 1,10-di-(N-carbazolyl)-4,6-decadiyne

A 2000 ml, three-necked, round bottom flask was fitted with mechanical stirrer, addition funnel, thermometer, Dry-Ice/acetone reflux condenser and means for providing nitrogen atmosphere. To the flask was added 10.4 g (0.062 mole) of carbazole, 3.27 g (0.068 mole) of sodium amide and 360 ml of liquid ammonia. The resulting mixture was stirred at −33° C. for 2.5 hr. The reaction mixture was cooled to −55° C. and a solution of 17.5 g (0.037 mole, 1.2 times theoretical) of 4,6-decadiyn-1,10-diol bis-p-toluenesulfonate (from Example 3A) in 15 ml of dry 1,2-dimethoxyethane was added dropwise over a period of 30 min. After stirring at −55° C. for an additional 5 hr, 1000 ml of hexane was added and the ammonia in the reaction was allowed to evaporate overnight. An additional 1000 ml of hexane was added to the reaction mixture, and the resulting mixture was vigorously stirred for about 1 hr. The hexane extract (fraction 1) was concentrated and dried, resulting in 2.9 g of solid, which was discarded. The remaining hexane-insoluble residue was extracted with ether at 500 ml per fraction. Removal of the solvent from each fraction gave the following results: fraction 2, 3.8 g (recrystallization from benzene/petroleum ether gave solids, m.p. at 248° C., which were discarded); fraction 3, 2.0 g (m.p. 144°–164° C.; recrystallization from acetone/petroleum ether gave 1.4 g of crystals, m.p. 168°–171° C.); fraction 4, 0.9 g (m.p. 164°–170° C.); and fractions 5 and 6, 2.5 g (m.p. 164°–170° C.). The solids obtained from fraction 4 (0.9 g) were recrystalized from 50 ml of 50% benzene/petroleum ether, giving 0.55 g of star-like, yellow crystals, m.p. 171°–172° C. I.R. (KBr pellet) in cm$^{-1}$: 3060 (Ar—H), 2930 (CH), 1630+1600 (aromatic C═C), 1480 (CH bending), 1440+1320 (CN stretching), 740+710 (Ar H). NMR (CDCl$_3$/TMS): δ 8.2–7.1 (complex m, Ar H, 8H), 4.40 (t, NCH$_2$, J≈6.5 Hz, 2H), 2.22 (m, CH$_2$CH$_2$C≡C, 4H). Anal: calculated for $C_{34}H_{28}N_2$: C, 87.90%; H, 6.07%; N, 6.07%; found: C, 87.87%; H, 6.32%; N, 5.63%.

EXAMPLE 4

Synthesis of 9-(N-carbazolyl)-5,7-nonadiyn-1-ol Monomer and Polymer

The synthesis of 9-(N-carbazolyl)-5,7-nonadiyn-1-ol was carried out by first preparing 6-bromo-5-hexyn-1-ol from 5-hexyn-1-ol and sodium hypobromite. The 6-bromo-5-hexyn-1-ol was then reacted with 3-(N-carbazolyl)-1-propyne to form the desired product. Details of the reactions are given below.

A. Synthesis of 6-bromo-5-hexyn-1-ol

A 1000 ml, three-necked, round bottom flask was equipped with mechanical stirrer, addition funnel, thermometer and means for providing nitrogen atmosphere. To the flask was added a solution of 32.8 g (0.82 mole) of sodium hydroxide in 165 ml of water. The solution was stirred and 58 g (0.36 mole) of bromine was added dropwise with cooling between 5° and 8° C. Subsequently, a solution of 20 g (0.204 mole) of 5-hexyn-1-ol in 100 ml of 1,2-dimethoxyethane was added dropwise over a period of 70 min at 9° to 11° C. After stirring at 8° to 12° C. for an additional 4 hr, the reaction mixture was poured into 200 ml of sodium chloride solution. The resulting mixture was extracted three times with 200 ml portions of ether. The combined ethereal layers were washed twice with 100 ml portions of water, dried over MgSO$_4$ and concentrated, resulting in 32 g of light yellow liquid. The crude product was purified by distillation, providing 25.3 g (72% yield) of colorless liquid, b.p. 60° C./0.05 mm. I.R. (film/neat) in cm$^{-1}$: 3350 (OH), 2950+2875 (CH), 2220 (C C), 1065+1050 (O—H bending and C—O stretching). Anal: calculated for $C_6H_9OBr$: C, 40.71%; H, 5.12%; found: C, 41.09%; H, 5.16%.

B. Synthesis of 9-(N-carbazolyl)-5,7-nonadiyn-1-ol

A 250 ml, three-neck, round bottom flask was fitted with mechanical stirrer, addition funnel, reflux condenser and means for providing nitrogen atmosphere. To the flask was added 20.5 g (0.10 mole) of 3-(N-carbazolyl)-1-propyne (prepared as in Example 2A), 0.7 g of hydroxylamine hydrochloride, 0.3 g of cuprous chloride, 100 ml of dimethylformamide, 17 ml of water and 17 ml of 70% ethylamine. The resulting mixture was stirred vigorously and a solution of 26.5 g (0.15 mole) of 6-bromo-5-hexyn-1-ol (from Example 4A) in 5 ml of dimethylformamide was added dropwise over a period of 25 min at 35°–40° C. The reaction was exothermic and the reaction temperature was controlled with a water bath. After heating at 35° to 40° C. for an additional 1.5 hr, the reaction mixture was cooled to room temperature and poured into 200 ml of sodium chloride solution. The resulting mixture was extracted four times with 200 ml portions of ether. The combined ethereal layers were washed four times with 100 ml portions of 0.6 N HCl solution, twice with 100 ml portions of sodium bicarbonate solution, dried and concentrated, resulting in 32.2 g of light yellow solid. The crude product was washed twice with 400 ml portions of hexane at room temperature to remove any unreacted reactants, resulting in 24 g (80% yield) of white material, m.p. 96° to 104° C. Recrystallization from 20% acetone/petroleum ether (b.p. 65°–110° C.) at a concentration of 0.02 g/ml gave yellow needles, m.p. 103° to 108° C. I.R. (KBr pellet) in cm$^{-1}$: 3300 (OH), 3050 (Ar—H), 2950+2880 (CH), 2260 (C≡C), 1600 (C═C), 1480 (CH$_2$), 1460+1320 (CN), 750+720 (Ar). Anal: calculated for $C_{21}H_{19}NO$: C, 83.69%; H, 6.35%; N, 4.65%; found: C, 83.94%; H, 6.53%; N, 4.48%.

C. Synthesis of Poly-9-(N-carbazolyl)-5,7-nonadiyn-1-ol

About 0.224 g of monomer crystals (crystallized from heptane at a concentration of 0.004 g/ml) was subjected to 50 Mrad of γ-radiation at a dose rate of 1 Mrad/hr, giving rise to copper-brown mass. Extraction of any unpolymerized monomer with 25 ml acetone at room temperature provided 0.055 g (25% conversion) of copper-brown fibers with metallic brilliancy. I.R. (KBr pellet): 3400 (OH), 3050 (Ar—H), 2930+2850 (CH), 1600 (C≡C), 1480 (CH$_2$), 1450+1320 (CN), 1050 (OH), 740+720 cm$^{-1}$ (Ar). Anal. calculated for (C$_{21}$H$_{19}$NO)$_x$: C, 83.69%; H, 6.35%; N, 4.65%. Found: C, 83.11%; H, 6.55%, N, 4.59%.

EXAMPLE 5

Synthesis of 9-(N-carbazolyl)-5,7-nonadiyn-1-ol octadecylurethane Monomer and Polymer A 250 ml, three-necked, round bottom flask was fitted with mechanical stirrer, addition funnel, thermometer and means for providing nitrogen atmosphere. To the flask was added 7.2 g (0.024 mole) of 9-(N-carbazolyl)-5,7-nonadiyn-1-ol (prepared as in Example 4B), 20 ml of 1,2-dimethoxyethane, 0.2 g of dibutyl-tin-di-2-ethylhexanoate and 2 ml of triethylamine. A solution of 9.0 g (0.030 mole) of octadecylisocyanate in 10 ml of 1,2-dimethoxyethane was added dropwise over a period of 5 min with vigorous stirring. The reaction temperature rose to 28° C. from 23° C. in 5 min and then subsided. After stirring at 40° C. for an additional 2 hr, 150 ml of heptane was added to the reaction mixture. The precipitate was collected by filtration, washed with heptane and dried, resulting in 13.0 g (91% yield) of the desired monomer, 9-(N-carbazolyl)-5,7-nonadiyn-1-ol octadecylurethane, m.p. 95°–97° C. I.R. (KBr pellet) in cm$^{-1}$: 3340 (NH stretching), 1692 (C=O), 1540 (NH bending), 1480 (CH$_2$), 1460+1320 (C—N), 1260 (C—O—C), 750+720 (Ar). Upon exposure to light, the colorless monomer turned pink.

About 6.3 g of 9-(N-carbazolyl)-5,7-nonadiyne-1-ol octadecylurethane (crystallized from 1,2-dimethoxy ethane/heptane) was subjected to 50 Mrad of γ-radiation at a dose rate of 1 Mrad/hr, resulting in a black-brown mass. Extraction of any unpolymerized monomer with 400 ml of hot methanol for 2.5 hr provided 5.0 g (80% conversion) of black-brown polymer. I.R. (KBr pellet) in cm$^{-1}$: 3330 (NH), 3050 (Ar H), 2930+2860 (CH), 1685 (C=O), 1600 (C≡C), 1535 (NH), 1460+1320 (C—N), 1260 (C—O—C), 750+720 (Ar). Raman: $\nu_{C\equiv C}$=2088 cm$^{-1}$; $\nu_{C=C}$=1468+1455+1427 cm$^{-1}$. Anal: calculated for (C$_{40}$H$_{56}$N$_2$O$_2$)$_x$: C, 80.49%; H, 9.46%; N, 4.69%; found: C, 79.95%; H, 9.59%; N, 4.42%.

About 0.5 g of the polymer in a powder form was placed between the plattens of a hydraulic press and pressed at about 6 tons/in$^2$ for about 2 min at 260° C., resulting in a shiny, dark red film.

EXAMPLES 6–15

Several monomers were prepared, following the procedure of Example 5. In each case, an excess of an isocyanate was reacted with 9-(N-carbazolyl)-5,7-nonadiyn-1-ol (synthesis as in Example 4) in the presence of dibutyl-tin-di-2-ethylhexanoate, triethylamine and 1,2-dimethoxyethane to form the monomer in solution. Precipitation of the monomer was accomplished using heptane, hexane or petroleum ether (30°–60° C.). The precipitated monomer was collected by filtration, washed with heptane, hexane or petroleum ether and dried. Table II below lists the reactants, the amount of reactants, the resulting monomer, the yield and the melting point.

Table II.

| | Preparation of Monomers. | | | | |
|---|---|---|---|---|---|
| Example | Reactant 1 | Reactant 2 | Resulting Monomer | % Yield | m.p., °C. |
| 6 | 9-(N-carbazolyl)-5,7-nonadiyn-1-ol, 0.012 mole | dodecylisocyanate, 0.015 mole | 9-(N-carbazolyl)-5,7-nonadiyn-1-ol dodecylurethane | 85 | 89–91 |
| 7 | 9-(N-carbazolyl)-5,7-nonadiyn-1-ol, 0.012 mole | octylisocyanate, 0.018 mole | 9-(N-carbazolyl)-5,7-nonadiyn-1-ol octylurethane | 87 | 96–98 |
| 8 | 9-(N-carbazolyl)-5,7-nonadiyn-1-ol, 0.012 mole | hexylisocyanate, 0.018 mole | 9-(N-carbazolyl)-5,7-nonadiyn-1-ol hexylurethane | 91 | 112–111 |
| 9 | 9-(N-carbazolyl)-5,7-nonadiyn-1-ol, 0.020 mole | butylisocyanate, 0.030 mole | 9-(N-carbazolyl)-5,7-nonadiyn-1-ol butylurethane | 90 | 126–127 |
| 10 | 9-(N-carbazolyl)-5,7-nonadiyn-1-ol, 0.012 mole | ethylisocyanate, 0.018 mole | 9-(N-carbazolyl)-5,7-nonadiyn-1-ol ethylurethane | 92 | 128–129 |
| 11 | 9-(N-carbazolyl)-5,7-nonadiyn-1-ol, 0.028 mole | methylisocyanate, 0.042 mole | 9-(N-carbazolyl)-5,7-nonadiyn-1-ol methylurethane | 90 | 133–135 |
| 12 | 9-(N-carbazolyl)-5,7-nonadiyn-1-ol, 0.020 mole | ethoxycarbonylmethylisocyanate, 0.030 mole | 9-(N-carbazolyl)-5,7-nonadiyn-1-ol ethoxycarbonylmethylurethane | 97 | 117–119 |
| 13 | 9-N-carbazolyl)-5,7-nonadiyn-1-ol, 0.020 mole | butoxycarbonylmethylisocyanate, 0.030 mole | 9-(n-carbazolyl)-5,7-nonadiyn-1-ol butoxycarbonylmethylurethane | 93 | 90 |
| 14 | 9-N-carbazolyl)-5,7-nonadiyn-1-ol, 0.020 mole | p-tolylisocyanate, 0.032 mole | 9-(N-carbazolyl)-5,7-nonadiyn-1-ol p-tolylurethane | 80 | 133–135 |
| 15 | 9-(N-carbazolyl)-5,7-nonadiyn-1-ol, 0.020 mole | m-tolylisocyanate, 0.035 mole | 9-(N-carbazolyl)-5,7-nonadiyn-1-ol m-tolylurethane | 87 | 110–113 |

Crystals of the monomer, typically crystallized from 1,2-dimethoxyethane in combination with heptane, hexane or petroleum ether (30°–60° C.), were then subjected to 50 Mrad of Co$^{60}$ γ-radiation at a dose rate of 1 Mrad/hr, as in Example 5, to form the corresponding polymer. Any unpolymerized monomer was extracted with hot methanol, enabling a determination to be made of the extent of conversion of monomer to polymer. Infrared and Raman spectra showed that polymerization had proceeded by 1,4-addition reaction in each case. In some instances, a small amount of the polymer in powder form was placed between the plattens of a hydraulic press and pressed at about 6 tons/in$^2$ for about 2 min at 280° C. to produce a film of the polymer. Photoconduction action spectra were measured of some polymer films to determine photoconduction action and onset. Table III below lists the percent conversion of the monomers (listed in Table II) to polymers, the color of the polymers, the color of the polymer films and the results of the photoconduction action spectra.

TABLE III.

| | | Conversion of Monomers to Polymers. | | |
|---|---|---|---|---|
| Example | % Conversion | Color of Polymer | Color of Polymer Film | Photoconduction Peaks, nm, and Onset, eV* |
| 6 | 87 | green-gold | green-gold (metallic luster) | — |
| 7 | 69 | " | dark green gold (metallic | — |
| 8 | 81 | orange-red | dark brown | 370 nm; 2.8 eV |
| 9 | 61 | black | " | — |
| 10 | 91 | " | " | — |
| 11 | (1) 91 | copper-like | copper-brown | — |
| | (2) 98** | gold colored fibers | — | |
| 12 | 47 | black | copper-brown | 370 nm; 2.8 eV |
| 13 | 42 | dark red | " | — |
| 14 | 48 | copper-brown | " | — |
| 15 | 85 | deep red | " | — |

*Measued in polymer films.
**Monomer was crystallized from acetone/petroleum etner prior to polymerization; unreacted monomer was extracted from polymer with acetone. Polymer was strongly dichroic, with repeat distance of 4.9 A along the chain, and non-centric.

EXAMPLE 16

Synthesis of 1,6-bis(N-3-bromocarbazolyl)-2,4-hexadiyne Monomer and Polymer Synthesis of 1,6-bis(N-3-bromocarbazolyl)-2,4-hexadiyne monomer was carried out by first preparing 3-bromocarbazole from carbazole and bromine. The product was converted to sodium 3-bromocarbazolide, which was then reacted with 3-bromo-1-propyne to give N-(2-propynyl)-3-bromocarbazole. Oxidative coupling of the propyne over cuprous chloride gave the desired monomer. Details of the reaction are given below.

A. Preparation of 3-bromocarbazole

A 250 ml, three-necked, round bottom flask was fitted with mechanical stirrer, addition funnel and reflux condenser (with drying tube). To the flask was added 16.7 g (0.10 mole) of carbazole and 100 ml of pyridine. The resulting mixture was stirred at 0° C. and 17.7 g (0.12 mole) of bromine was added dropwise over a period of 35 min. After stirring at 0° C. for an additional 1 hr, the resulting red mixture was poured into 600 ml of 3 N—HCl solution. The resulting precipitate was collected by filtration, washed with 200 ml of water, twice with 100 ml portions of 5% NaOH solution, and three times with 250 ml portions of water. The crude product was dissolved in 1500 ml of ether and dried over magnesium sulfate. Concentration of the ethereal solution gave 22.7 g (85% yield) of powder, m.p. 179°–183° C. Recrystallization three times from methanol gave 8.7 g of the desired product, m.p. 200°–201° C.

B. Synthesis of N-(2-propynyl)-3-bromocarbazole

A 500 ml, three-necked, round bottom flask was fitted with mechanical stirrers, thermometer, Dry Ice/acetone reflex condenser (with KOH drying tube) and addition funnel. To the flask was added 210 ml of liquid ammonia and 8.7 g (0.035 mole) of 3-bromocarbazole (from Example 16A). To this mixture was added 1.52 g (0.039 mole) of sodium amide at −33° C. The resulting mixture was stirred mechanically at −33° C. for 3 hr. The mixture was then cooled to −55° C. and 5.9 g (0.049 mole) of 3-bromo-1-propyne was added dropwise over a period of 20 min. After stirring at −55° C. for an additional 5 hr, the ammonia was allowed to evaporate overnight. The residue was extracted three times with 300 ml portions of benzene. Concentration of the combined benzene extractants gave 9.5 g (95% yield) of light yellow powder, m.p. 142°–149° C. Recrystallization from methanol gave colorless needle crystals, m.p. 155°–157° C. I.R. (KBr pellet) in cm$^{-1}$: 3300 (C≡CH), 3070 (Ar—H), 2940 (CH), 2140 (C≡C), 1630+1600 (C=C), 1455+1330 (CN), 800+740+720 (Ar), 680+660 (C≡CH). Anal: calculated for $C_{15}H_{10}NBr$: C, 63.40%; H, 3.55%; N, 4.93%; found: 63.37%; H, 3.35%; N, 4.83%.

C. Synthesis of 1,6-bis(N-3-bromocarbazolyl)-2,4-hexadiyne

A 100 ml, three-necked, found bottom flask was fitted with mechanical stirrer, reflex condenser, thermometer and oxygen gas inlet and outlet. To the flask was added 2.7 g (0.0095 mole) of N-(2-propynyl)-3-bromocarbazole (from Example 16B), 25 ml of p-dioxane, 0.1 g of cuprous chloride and 0.12 g of N,N,N',N'-tetramethylenediamine. The resulting mixture was stirred and oxygen was introduced to the mixture. The reaction temperature rose to 35° C. from 26° C. in 10 min and then subsided. After stirring and introduction of oxygen for an additional 4.5 hr, the mixture was concentrated to near dryness, and 25 ml of 0.6 N HCl solution was added to the mixture. The resulting white precipitate was collected by filtration, washed three times with 25 ml portions of water, twice with 25 ml portions of methanol, twice with 25 ml portions of ether and dried, resulting in 2.6 g (96% yield) of product, m.p. 255°–257° C. (decomposed). Recrystallization once from toluene gave needle-like crystals, m.p. 260°–261° C. I.R. (KBr pellet) in cm$^{-1}$: 3050 (Ar—H), 2920 (CH), 1620+1600 (C=C), 1445+1320 (C—N), 790+740+720 (Ar). Anal: calculated for $C_{30}H_{18}N_2Br_2$: C, 63.63%; H, 3.20%; N, 4.95%; found: C, 64.16%; H, 3.33%; N, 5.06%.

D. Solid State Polymerization of 1,6-bis(N-3-bromocarbazolyl)-2,4-hexadiyne Mechanical stress: Upon compressing at a pressure of about 20,000 lb/in$^2$, the colorless monomer crystals turned blue, indicating that they were solid state polymerizable upon mechanical stress.

γ-irradiation polymerization: The needle-like colorless crystals were subjected to 40 Mrad of γ-radiation at a dose rate of 1 Mrad/hr at about 110° C., resulting in blue-colored crystals.

EXAMPLE 17

Synthesis of 1-(N-Carbazolyl)-2,4-heptadecadiyne Monomer and Polymer

A. Synthesis of 1-Bromo-1-tetradecyne.

A 250 ml, three-necked, round bottom flask was fitted with mechanical stirrer, thermometer, addition funnel and means for providing nitrogen atmosphere. To the flask was added 41 ml (0.10 mole) of 2.4 M butyl lithium/hexane solution and 40 ml of anhydrous ether. The resulting mixture was stirred vigorously and 17.2 g (0.090 mole) of tetradecyne was added over a period of 25 min at −10° C. After stirring at −10° to −15° C. for an additional 35 min, the reaction mixture was cooled in a Dry Ice/acetone bath. About 16.0 g (0.10 mole) of bromine was added dropwise over a period of 90 min at −60° C. to −68° C. After stirring at −40° C. for an additional 40 min, the reaction mixture was poured into 100 ml of water. The resulting mixture was extracted twice with 50 ml portions of ether. The combined ethereal layers were washed twice with 50 ml portions of sodium bicarbonate solution, dried, and concentrated, resulting in 21.9 g (80% yield) of light yellow liquid. I.R. (film/neat) in cm$^{-1}$: 2230 (C≡C), 1470 (CH$_2$), 720 [—(CH$_2$)$_n$—, n≧4].

B. Synthesis of 1-(N-carbazolyl)-2,4-heptadecadiyne

A 250 ml, three-necked, round bottom flask was fitted with mechanical stirrer, addition funnel, reflux condenser, thermometer and means for providing nitrogen atmosphere. To the flask was added 0.5 g of hydroxylamine hydrochloride, 0.25 g of cuprous chloride, 15.0 g (0.073 mole) of 3-(N-carbazolyl) propyne (prepared as in Example 2A), 75 ml of dimethylformamide, 12 ml of water, and 12 ml of 70% ethylamine. The resulting mixture was stirred and heated to 37° C., and 21.9 g (0.080 mole) of 1-bromo-1-tetradecyne (from Example 17A) was added dropwise over a period of 30 min at a temperature of 37° to 52° C. After stirring and heating at 50° to 55° C. for an additional 75 min, the reaction mixture was cooled to room temperature and poured into an aqueous solution of 150 ml of sodium chloride containing 5 ml of concentrated HCl. The resulting mixture was extracted four times with 100 ml portions of ether. The combined ethereal layers were washed ten times with 50 ml portions of 0.6 N HCl, twice with 50 ml portions of sodium bicarbonate, dried and concentrated, resulting in 28.0 g (96% yield), of yellow powder, m.p. 53°–58° C. Recrystallization once from methanol gave colorless long needle crystals, m.p. 71°–72° C. I.R. (KBr Pellet) in cm$^{-1}$: 3060 (Ar—H), 2920+2850 (CH), 2260 (C≡C), 1620+1600 (C=C), 1480 (CH$_2$), 1460+1330 (CN), 750+720 (Ar H). Anal: Calculated for C$_{29}$H$_{35}$N: C, 87.60%; H, 8.87%; N, 3.52%; found: C, 88.32%; H, 8.72%; N, 3.45%.

C. Solid State Polymerization of 1-(N-carbazolyl)-2,4-heptadecadiyne

The colorless long needle crystals (crystallized from methanol) were subjected to 50 Mrad of γ-radiation at a dose rate of 1 Mrad/hr, resulting in copper-brown crystals comprising a mixture of monomer and polymer.

What is claimed is:

1. A polymer prepared by 1,4-addition reaction from a monomer having the formula

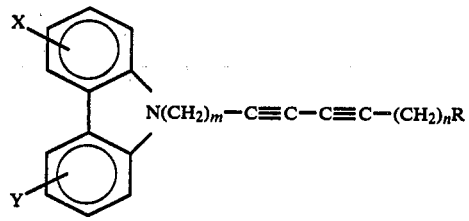

where "m" and "n" are integers of from 0 to 10, X and Y are independently selected from the group consisting of —H, —Cl, —Br and —NO and R is a member selected from the group consisting of —CH$_3$ —OH, —OCONHR' and

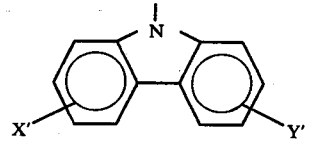

where R' is (a) an alkyl derivative represented by —C$_r$H$_{2r+1}$, where "r" ranges from 1 to 18, (b) an aryl derivative of —C$_6$H$_4$, —C$_6$H$_4$—p—CH$_3$, —C$_6$H$_4$—m—CH$_3$ or —C$_{10}$H$_7$ or (c) an ester derivative of —CH$_2$OCOC$_s$H$_{2s+1}$, where "s" ranges from 2 to 4 and X' and Y' are independently selected from the group consisting of —H, —Cl, —Br and —NO.

2. The polymer of claim 1 in which R is a member selected from the group consisting of —CH$_3$, —OH, —OCONHR' and

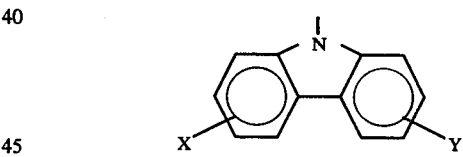

3. The polymer of claim 2 in which X and Y are independently selected from the group consisting of —H and —Br.

4. The polymer of claim 3 in which X and Y are both —H.

5. The polymer of claim 2 in which "m" and "n" are equal to each other and range from 0 to 4.

6. The polymer of claim 5 in which R is

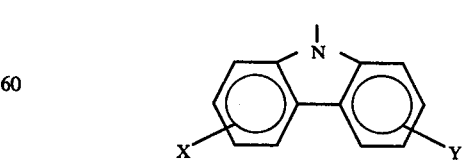

7. The polymer of claim 6 in which "m" and "n" are both 1.

8. The polymer of claim 7 in which the monomer has the formula

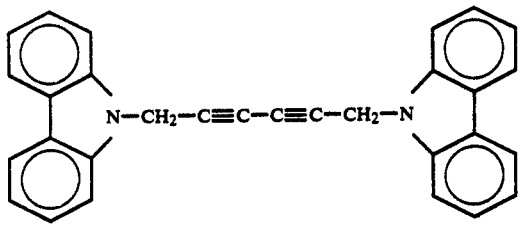

9. The polymer of claim 1 in which "m" and "n" are unequal to each other and range from 1 to 4.

10. The polymer of claim 9 in which R is a member selected from the group consisting of —CH₃, —OH and —OCONHR'.

11. The polymer of claim 10 in which the monomer has the formula

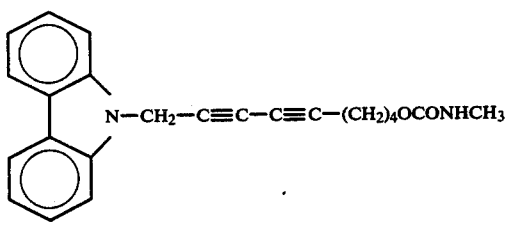

12. A photoconductor comprising a polymer formed by 1,4-addition reaction from a monomer having the formula

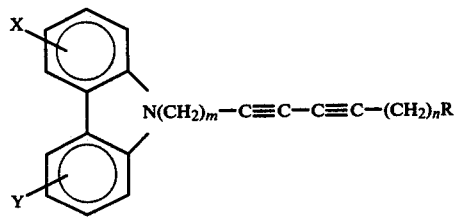

where "m" and "n" are integers of from 0 to 10, X and Y are independently selected from the group consisting of —H, —Cl, —Br and —NO and R is a member selected from the group consisting of —CH₃, —OH, —OCONHR' and

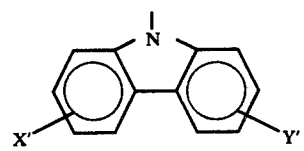

where R' is (a) an alkyl derivative represented by —C$_r$H$_{2r+1}$, where "r" ranges from 1 to 18, (b) an aryl derivative of —C₆H₅, —C₆H₄—p—CH₃, —C₆H₄—m—CH₃ or —C₁₀H₇ or (c) an ester derivative of —CH₂OCOC$_s$H$_{2s+1}$, where "s" ranges from 2 to 4 and X' and Y' are independently selected from the group consisting of —H, —Cl, —Br and —NO.

13. The photoconductor of claim 12 in which the monomer has the formula

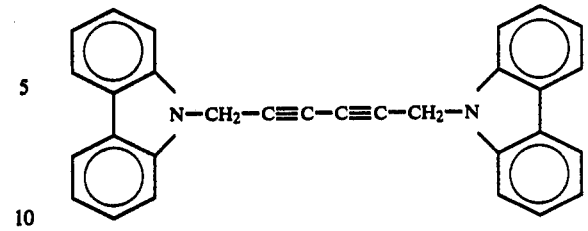

14. A non-linear optical device comprising a polymer formed by 1,4-addition reaction from a monomer having the formula

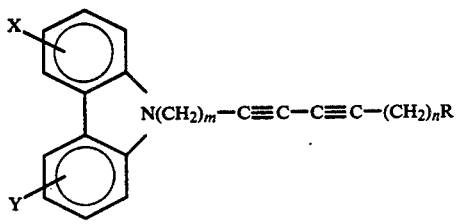

where "m" and "n" are integers of from 0 to 10, X and Y are independently selected from the group consisting of —H, —Cl, —Br and —NO and R is a member selected from the group consisting of —CH₃, —OH, —OCONHR' and

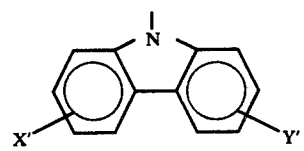

where R' is (a) an alkyl derivative represented by —C$_r$H$_{2r+1}$, where "r" ranges from 1 to 18, (b) an aryl derivative of —C₆H₅, —C₆H₄—p—CH₃, —C₆H₄—m—CH₃ or —C₁₀H₇ or (c) an ester derivative of —CH₂OCOC$_s$H$_{2s+1}$, where "s" ranges from 2 to 4 and X' and Y' are independently selected from the group consisting of —H, —Cl, —Br and —NO.

15. The device of claim 14 in which the monomer has the formula

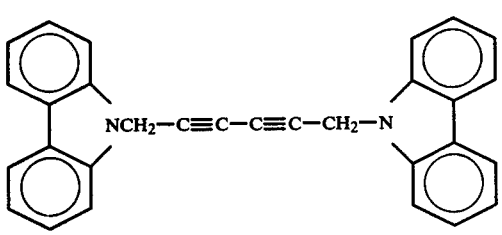

16. The device of claim 14 in which the monomer has the formula

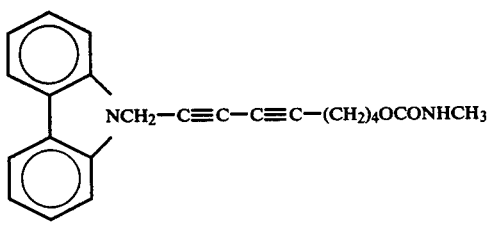

* * * * *